United States Patent

Atsumi et al.

[11] Patent Number: 5,833,959
[45] Date of Patent: Nov. 10, 1998

[54] COMPOSITIONS FOR DENTAL TISSUE

[75] Inventors: Kiminori Atsumi; Tsutomu Ishizaki; Hiroyuki Kawamata, all of Tokyo, Japan

[73] Assignee: Sangi Co., Ltd., Japan

[21] Appl. No.: 786,923

[22] Filed: Jan. 23, 1997

[30] Foreign Application Priority Data

Jan. 24, 1996 [JP] Japan .................................. 8-028704

[51] Int. Cl.⁶ ..................................................... A61K 7/16
[52] U.S. Cl. ............................. 424/57; 424/49; 424/401; 433/228.1; 423/308; 106/35
[58] Field of Search ........................ 424/49–58; 423/308, 423/369; 433/228.1; 106/35

[56] References Cited

U.S. PATENT DOCUMENTS

| | | | |
|---|---|---|---|
| 3,829,562 | 8/1974 | Kim et al. | 424/57 |
| 4,327,079 | 4/1982 | Aoki | 424/57 |
| 4,342,741 | 8/1982 | Aoki | 424/57 |
| 4,933,171 | 6/1990 | Bristow et al. | 424/57 |
| 4,933,173 | 6/1990 | Bristow et al. | 424/57 |
| 4,988,499 | 1/1991 | Bristow et al. | 424/57 |
| 5,009,898 | 4/1991 | Sakuma et al. | 106/35 |
| 5,089,254 | 2/1992 | Coulson | 424/57 |
| 5,112,597 | 5/1992 | Coulson | 424/57 |
| 5,135,396 | 8/1992 | Kuhokl | 424/49 |
| 5,158,756 | 10/1992 | Ogawa et al. | 423/309 |
| 5,217,699 | 6/1993 | Tagaya et al. | 423/300 |
| 5,268,174 | 12/1993 | Sakuma et al. | 424/57 |
| 5,650,176 | 7/1997 | Lee et al. | 424/642 |

FOREIGN PATENT DOCUMENTS

| | | | |
|---|---|---|---|
| 0029332 | 5/1981 | European Pat. Off. | A61K 7/16 |
| 0165454 | 12/1985 | European Pat. Off. | A61K 7/16 |
| 0342746 | 11/1989 | European Pat. Off. | A61K 7/18 |
| 1-32203 | 6/1989 | Japan . | |

OTHER PUBLICATIONS

"Sub–micrometer Hydroxyapatite Bioceramics", Zeng, et al, Chemical Abstracts, vol. 119, No. 13, Abstract No. 133875m, Sep. 27, 1993.

"Dentifice compsn.–contg. anhidrous calcium hydrogen phosphate and sucrose fatty acid ester as surfactant", Database WPI, Week 8545, JP–A–60188308, Sep. 25, 1985 Shika Journal 39(6): pp. 809–822, 1994.

Primary Examiner—Shep K. Rose
Attorney, Agent, or Firm—Ladas & Parry

[57] ABSTRACT

A composition for use in dental tissues includes hydroxyapatite having a particle size in a range from about 0.05 $\mu$m to about 1.0 $\mu$m. The amount of the hydroxyapatite is preferably a minimum of 0.1 percent by weight.

6 Claims, 8 Drawing Sheets

COMPOSITIONS FOR DENTAL TISSUE

BACKGROUND OF THE INVENTION

1. Field of the Invention

The present invention generally relates to compositions for use in dental tissues and, more particularly, the present invention relates to a composition which is capable of repairing pits present on a tooth surface and protecting the tooth afterward, preventing tooth decay, strengthening teeth, and whitening teeth surfaces.

2. Description of the Related Art

There are two group types—acidic group and basic group—present in proteins contained in saliva. The former has a high affinity for calcium contained in a hydroxyapatite molecule and the latter has a high affinity for a phosphate group also contained in the hydroxyapatite molecule. Proteins derived from saliva also have a high affinity for a hydroxyapatite molecule. Hydroxyapatite (hereinafter also referred to as HAp), expressed by a chemical formula of $Ca_{10}(PO_4)_6(OH)_2$, is one of the main components of mammalian teeth or bones and so superior in the affinity to living tissue that it is easily assimilated by the tissues of living body.

When the proteins derived from saliva or glycoproteins are absorbed on dentin which contains the hydroxyapatite molecules and the tooth surface is covered by such proteins, pericle is formed. Therefore, the enamel of a tooth is always covered by the pericle in an oral cavity. Now, dental caries are formed by the process in which bacteria adhere to the tooth surface, especially in pits and other harbored areas, to form plaque. Dental plaques are formed on the pericle, and 70% of its volume is said to comprise bacteria that are able to remain attached to the tooth surface. The rest of the 30% of its volume is said to be materials derived from the bacteria inhabiting the oral cavity. Colonies of bacteria attached to the tooth surface usually extend in a vertical direction along a tooth axis. Also, dental plaque located on a periphery of gum extend from a gingival crevice in a root tip direction. As a result, a gingival pocket is formed and a subgingival plaque (calculus), which is a bacterial deposit, is formed therein. The subgingival plaque thus formed is a main cause of decay of the tooth, i.e. dental caries and periodontal diseases.

Among the bacteria inhabiting the oral cavity, some bacteria with their enzymes are capable of acting on fermentable foods to form acids when they metabolize residual materials remaining in the oral cavity. The acids thus produced are the main cause of a dental decalcification. Also, some bacteria inhabiting the oral cavity produces endotoxin which causes inflammation of various kinds. Typical examples of such bacteria include *B.gingivalis, E.corrodens, A.viscosus* and Capnocytophaga. When such endoteric bacteria increase in the dental plaques located on a periphery of the gum, gingivitis is caused and if they are proliferated in the subgingival plaque, periodontium is damaged and the inflammation thereof is caused. Moreover, active anaerobic bacteria in the gingival pocket metabolizes proteins and produces such materials as hydrogen sulfide and methyl mercaptan, which may be a cause of halitosis. Thus, since plaques can be a cause of the dental caries, periodontal disease and halitosis, it is preferable to remove them in an early stage of the formation.

Various kinds of tooth brushing agents including paste, liquid and powder type have been used as a means for removing dental plaques. These days, the tooth brushing agents have function not only for removing dental plaques but also for antibacterial activity, plaque deposition inhibitory, recalcification (remineralization) and teeth strength enhancement.

The term "antibacterial activity" of a tooth brushing agent means an effect of killing bacteria involving the plaque formation, and triclosan and chlorhexidine are known compounds having such effect. The term "plaque deposition inhibitory" means an effect of preventing a formation of plaques, and dextranase and fluorine are known for having such effect. The term "recalcification" means an effect of promoting deposition of calcium phosphate on the enamel of a tooth and prevents a slow progression of a dental caries. The term "teeth strength enhancement" means an effect of increasing resistance of an enamel of a tooth against acids. Because one the primary components of tooth mineral is hydroxyapatite, the incorporation of additional hydroxyapatite into dental enamel can, in effect, remineralize demineralized tooth material. Thus, hydroxyapatite is known for having the remineralization effect and the teeth strength enhancement effect.

Although the use of a compound having the antibacterial activity can reduce the number of bacteria, it is not possible to completely kill the bacteria in the oral cavity, and hence fermentable foods are metabolized by the bacteria and dental caries slowly progress. The use of a compound having the plaque deposition inhibitory activity is effective for inhibiting dental caries and preventing periodontal diseases, however, the compound cannot repair minute scratches caused by brushing of the teeth or pits caused by decalcification due to slow dental caries. That is, the use of a compound having the antibacterial activity or the plaque deposition inhibitory activity has little effect on repairing the scratches or pits formed on the tooth surface.

As mentioned above, fluorine has the effect of recalcification and teeth strength enhancement. This is carried out by bonding of fluorine atoms to hydroxyapatite molecules which exist on the enamel of a tooth to form fluoroapatite molecules which may be expressed by the chemical formula of $Ca_{10}(PO_4)_6F_2$. Although the resistance of fluoroapatite against acids is better than that of hydroxyapatite, the color of fluoroapatite is somewhat blackish and, therefore, the tooth brushing agents containing fluorine have a disadvantage in their whitening effect. In addition, when fluorine is used, $Ca^{2+}$ and $PO_4^{3-}$ involving the recalcification are derived only from saliva.

Hydroxyapatite also has the recalcification and teeth strength enhancement effects as mentioned above. It is considered that hydroxyapatite molecules fill the pits or scratches on the surface of the teeth and promote recalcification of the enamel which has been decalcified due to dental caries, etc. Since the constituents of it is the same as that of the enamel of a tooth, hydroxyapatite has the effect of whitening the teeth. The effect of hydroxyapatite used in a tooth brushing agent has been confirmed in clinical testing (Shika Journal 39 (6): 809–822, 1994). Also, Japanese Laid-Open Patent Application No.1-32203 discloses a tooth brushing agent containing hydroxyapatite.

However, it has not been known that the degree of recalcification varies depending on a particle size of hydroxyapatite contained in a tooth brushing agent.

SUMMARY OF THE INVENTION

It is a general object of this invention to provide a composition for use in dental tissues in which the above-mentioned problem is eliminated.

A more specific object of the present invention is to provide a composition for use in dental tissues which is capable of repairing pits present on a tooth surface and protecting the tooth afterward, preventing tooth decay, strengthening teeth, and whitening the tooth surface.

Another object of the present invention is to provide a tooth brushing agent which is capable of repairing pits present on a tooth surface and protecting the tooth afterward, preventing tooth decay, strengthening teeth, and whitening the tooth surface.

The objects described above are achieved by a composition for dental tissue comprising hydroxyapatite having a particle size of a maximum of about 1.0 μm.

The objects described above are also achieved by the composition for dental tissue comprising hydroxyapatite having a particle size in a range from about 0.05 μm to about 1.0 μm.

The objects described above are also achieved by the composition for dental tissue, wherein the amount of the hydroxyapatite is a minimum of 0.1 percent by weight.

The objects described above are also achieved by the composition for dental tissue, wherein at least one adjuvant selected from a group consisting of abrasives, humectants, surfactants, tackiness agents, preservatives, sweetening, flavors, calcification-promoting protein, fluorine and polymers, is included in the composition.

According to the above composition for dental tissue, since hydroxyapatite has the recalcification and teeth strength enhancement effects, it is considered that hydroxyapatite molecules fill the pits or scratches on the teeth surface and promote recalcification of the enamel which has been decalcified due to dental caries, etc. Thus, pits present on a tooth surface may be repaired and the teeth are protected thereafter. Also, tooth decay may be prevented and teeth are strengthen and whitened.

The objects described above are achieved by a tooth brushing agent comprising hydroxyapatite having a particle size of a maximum of about 1.0 μm.

The objects described above are achieved by the tooth brushing agent comprising hydroxyapatite having a particle size in a range from about 0.05 μm to about 1.0 μm.

The objects described above are also achieved by the tooth brushing agent, wherein the amount of the hydroxyapatite is a minimum of 0.1 percent by weight.

The objects described above are also achieved by the tooth brushing agent, wherein at least one adjuvant selected from a group consisting of abrasives, humectants, surfactants, tackiness agents, preservatives, sweetening, flavors, calcification-promoting protein, fluorine and polymers, is included in the tooth brushing agent.

According to the above tooth brushing agent, since hydroxyapatite has the recalcification and teeth strength enhancement effects, it is considered that hydroxyapatite molecules fill the pits or scratches on the teeth surface and promote recalcification of the enamel which has been decalcified due to dental caries, etc. Thus, pits present on a tooth surface may be repaired and the teeth are protected thereafter. Also, tooth decay may be prevented and teeth are strengthen and whitened.

The objects described above are achieved by a composition for dental tissue comprising calcium tertiary phosphate having a particle size of a maximum of about 1.0 μm.

The objects described above are achieved by the composition for dental tissue comprising calcium tertiary phosphate having a particle size in a range from about 0.05 μm to about 1.0 μm.

The objects described above are also achieved by the composition for dental tissue, wherein the amount of the calcium tertiary phosphate is a minimum of 0.1 percent by weight.

The objects described above are also achieved by the composition for dental tissue, wherein at least one adjuvant selected from a group consisting of abrasives, humectants, surfactants, tackiness agents, preservatives, sweetening, flavors, calcification-promoting protein, fluorine and polymers, is included in the composition.

According to the above composition for dental tissue, since calcium tertiary phosphate has the recalcification and teeth strength enhancement effects, it is considered that calcium tertiary phosphate molecules fill the pits or scratches on the surface of the teeth and promote recalcification of the enamel which has been decalcified due to dental caries, etc. Thus, pits present on a tooth surface may be repaired and the teeth are protected thereafter. Also, tooth decay may be prevented and teeth are strengthen and whitened.

The objects described above are achieved by a tooth brushing agent comprising calcium tertiary phosphate having a particle size of a maximum of about 1.0 μm.

The objects described above are achieved by the tooth brushing agent comprising calcium tertiary phosphate having a particle size in a range from about 0.05 μm to about 1.0 μm.

The objects described above are also achieved by the tooth brushing agent, wherein the amount of the calcium tertiary phosphate is a minimum of 0.1 percent by weight.

The objects described above are also achieved by the tooth brushing agent, wherein at least one adjuvant selected from a group consisting of abrasives, humectants, surfactants, tackiness agents, preservatives, sweetening, flavors, calcification-promoting protein, fluorine and polymers, is included in the tooth brushing agent.

According to the above tooth brushing agent, since calcium tertiary phosphate has the recalcification and teeth strength enhancement effects, it is considered that calcium tertiary phosphate molecules fill the pits or scratches on the surface of the teeth and promote recalcification of the enamel which has been decalcified due to dental caries, etc. Thus, pits present on a tooth surface may be repaired and the teeth are protected thereafter. Also, tooth decay may be prevented and teeth are strengthen and whitened.

Other objects and further features of the present invention will be apparent from the following detailed description with reference to the accompanied drawings.

DESCRIPTION OF THE PREFERRED EMBODIMENTS

In the following, a principle and embodiments of the present invention will be described in detail with reference to the accompanying drawings.

The compounds for dental tissues according to the present invention may be prepared by mixing the above-mentioned hydroxyapatite and/or calcium tertiary phosphate (also referred to as calcium phosphate) with other components using an ordinary method, and forming the mixture into a tooth paste, tooth liquid, tooth powder, etc. Additives such as abrasives, humectants, surfactants, tackiness agents, preservatives, sweetening, flavors, and others which do not deteriorate the effect of the present invention may be used in a pharmaceutically acceptable amount.

Examples of such additives are as follows:

Abrasives: calcium carbonate, calcium pyrophosphate, silicic anhydride, aluminium silicate, aluminium hydroxide, calcium hydrogenphosphate, etc.

Humectants: glycerin, sorbitol, propylene glycol, polyethylene glycol, dipropylene glycol, maltitol, etc.

Surfactants: salts of alkylsulfate, salts of alkylbenzenesulfonate, sucrose-fatty acid ester, sodium laurylsulfate, etc.

Tackiness (binder) agents: hydroxyethyl cellulose, sodium carboxymethyl cellulose, carageenan, carboxy vinyl polymer, poly(sodium acrylate), xanthan gum, etc.

Preservatives: sodium benzoate, methyl parapene, paraoxy benzoate, alkyldiaminoethylglycine hydrochloride, etc.

Sweetening: sodium saccharin, xylitol, stevioside, etc.

Flavors: menthol, orange oil, spearmint oil, peppermint oil, lemon oil, eucalyptus oil, methyl salicylate, etc.

Others: allantoin, tocopherol acetate, isopropyl phenol, β-glycyrrhetinic acid, triclosan, chlorhexidine, dextranase, chlorophyll, flavonoid, tranexamic acid, hinokitiol, halitosis removers, tooth detinter, etc.

The compound for dental tissues according to the present invention is comprised of hydroxyapatite and/or calcium tertiary phosphate having a particle size of a maximum of about 1.0 µm and other suitable additives as mentioned above. The amount of hydroxyapatite and calcium tertiary phosphate contained in the compound for dental tissues according to the present invention is preferably a minimum of about 0.1%. If the amount is less than about 0.1%, it is difficult for the hydroxyapatite and/or calcium tertiary phosphate molecules to contact decalcified portions or scratched portions on the teeth, and hence the effect of the present invention may not be easily obtained.

Particles of hydroxyapatite and/or calcium tertiary phosphate may be obtained by grinding the compound using an appropriate conventional mill or pulverizer. Then, the particles are mixed with suitable amounts of additives as mentioned above to be produced as a paste, liquid or powder form. Any mixing procedures appropriate for the purpose may be used.

When the compound for use in oral tissues or the tooth brushing agent according to the present invention is applied, recalcification of the teeth by hydroxyapatite and/or calcium tertiary phosphate is further promoted due to the presence of saliva in the oral cavity. The reason of this is considered to be due to the presence of calcification-promoting proteins such as phosvitin, casein and histidine-rich protein. Thus, the compound for use in oral tissues or the tooth brushing agent according to the present invention may be used with such calcification-promoting proteins.

It is also possible to reinforce the teeth by applying the compound for use in oral tissues or the tooth brushing agent according to the present invention on the surfaces thereof, followed by the application of fluoride. It is preferable to apply the compound for use in oral tissues or the tooth brushing agent according to the present invention and the above-mentioned calcification-promoting proteins and, thereafter, apply fluoride thereon using a conventional method. It is also possible to apply the compound of the present invention on the surface of the teeth and thereafter cover the site with a polymer for a protection. Any know polymers suitable for the purpose may be used using a conventional method.

EXAMPLES

A description will be given of examples of the present invention. The term "percent" used below means "percent by weight" unless otherwise indicated.

Example 1
Comparison of recalcification when a particle size is varied
(1) Production of artificial dental caries on human teeth Four enamel blocks were prepared from a human impacted third molar tooth, and a window of 3 mm diameter was formed on the enamel surface. These samples were immersed in a lactated buffer (pH 4.5) at 37° C. for 72 hours to form artificial dental caries.
(2) Comparison using hydroxyapatite having different particle sizes Experiments were conducted, using the above enamel blocks, on the effect of hydroxyapatite on recalcification by varying the particle size of hydroxyapatite. Hydroxyapatite was grounded until its particle size became about 0.05 to 1.0 $\mu$m using a DYNO-MiLL, type KD-6 (Swiss WAB Co.). The particles of hydroxyapatite obtained was made into a slurry for the experiment which followed.

The above mentioned enamel blocks were immersed in three different kinds of solutions for 24 hours, namely, (a) artificial saliva (control), (b) HAp slurry of a maximum of about 1.0 $\mu$m particle size and (c) HAp slurry of more than about 1.0 $\mu$m particle size, each of which was maintained 37° C. The changes on the surface of each of the enamel blocks were observed under an electron microscope.
(3) Comparison using calcium tertiary phosphate having different particle sizes Experiments were conducted, using the above enamel blocks, on the effect of calcium tertiary phosphate on recalcification by varying the particle size of calcium tertiary phosphate.

Figure 1A:
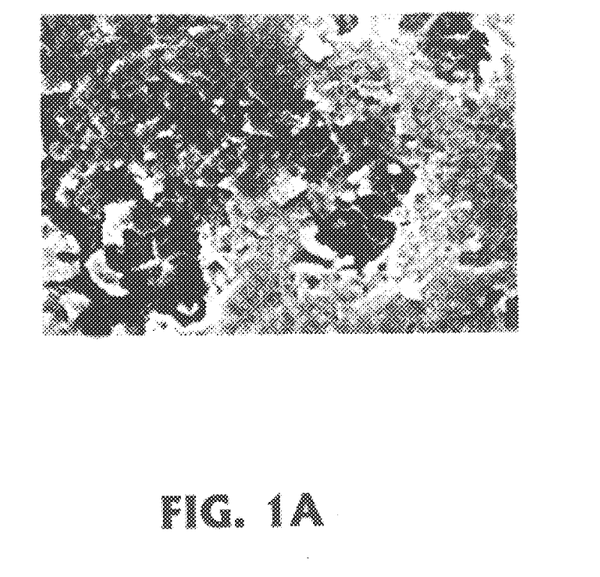
FIG. 1A is a photograph taken on a magnified scale (×3000) under an electron microscope showing the surface of an enamel block prepared from a human impacted third molar tooth, on which artificial dental caries were generated.
Figure 1B:
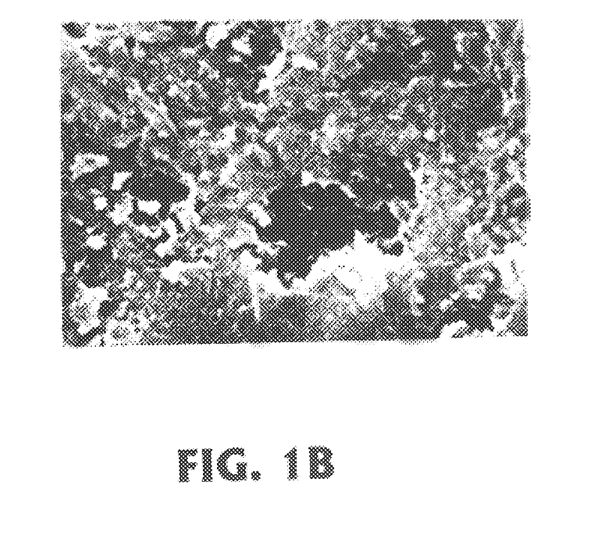
FIG. 1B is a photograph taken on a magnified scale (×3000) under an electron microscope showing the surface of an enamel block prepared from a human impacted third molar tooth, on which artificial dental caries were generated and then immersed in an artificial saliva solution.
Figure 1C:
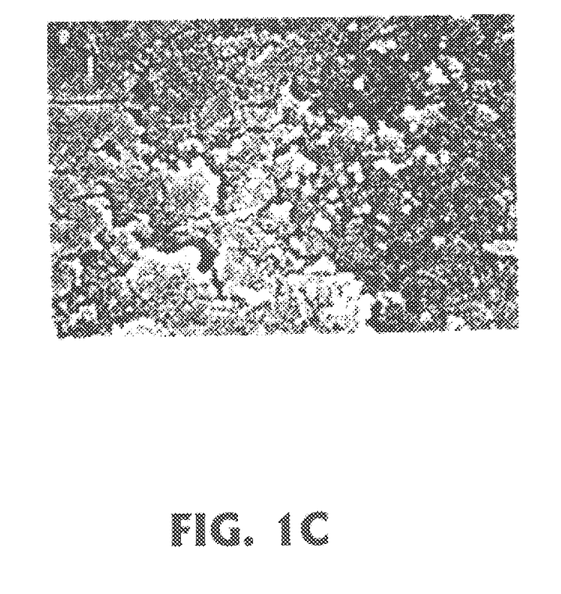
FIG. 1C is a photograph taken on a magnified scale (×3000) under an electron microscope showing the surface of an enamel block prepared from a human impacted third molar tooth, on which artificial dental caries were generated and then immersed in a HAp slurry having a particle size of a maximum of 1.0 μm.
Figure 1D:
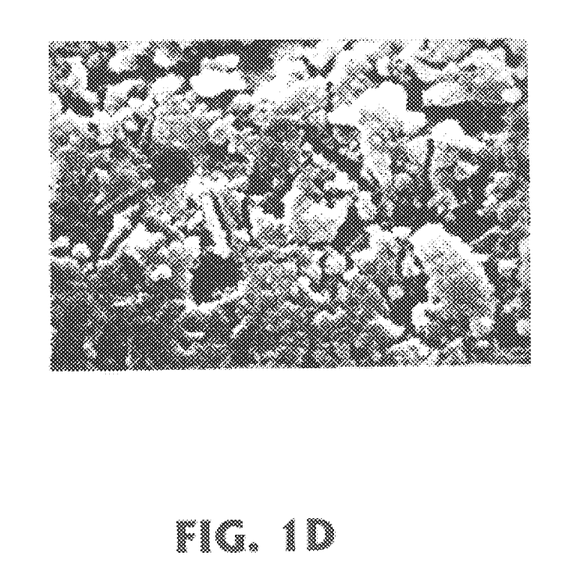
FIG. 1D is a photograph taken on a magnified scale (×3000) under an electron microscope showing the surface of an enamel block prepared from a human impacted third molar tooth, on which artificial dental caries were generated and then immersed in a HAp slurry having a particle size of more than 1.0 µm.
Figure 2A:
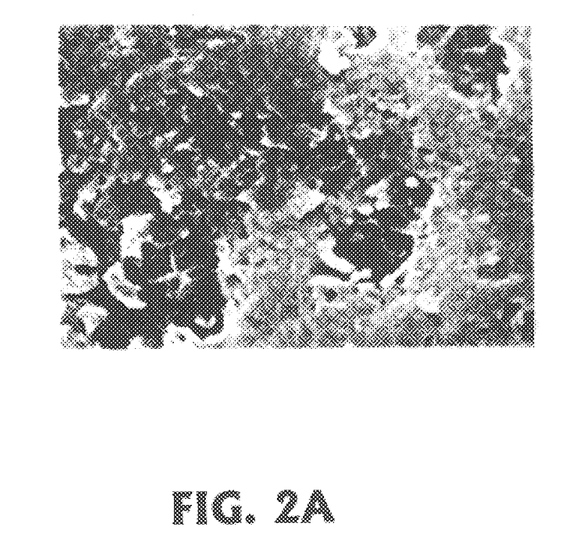
FIG. 2A is a photograph taken on a magnified scale (×3000) under an electron microscope showing the surface of an enamel block prepared from a human impacted third molar tooth, on which artificial dental caries were generated.
Figure 2B:
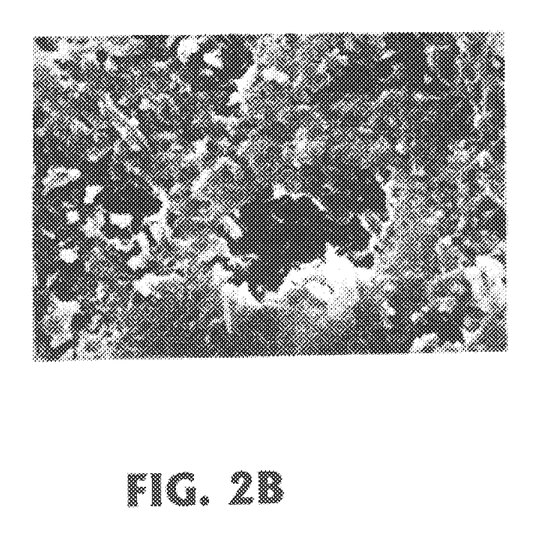
FIG. 2B is a photograph taken on a magnified scale (×3000) under an electron microscope showing the surface of an enamel block prepared from a human impacted third molar tooth, on which artificial dental caries were generated and then immersed in an artificial saliva solution.
Figure 2E:
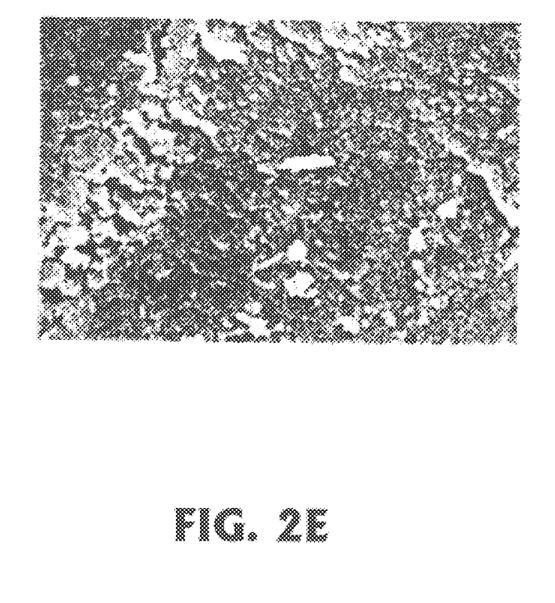
FIG. 2E is a photograph taken on a magnified scale (×3000) under an electron microscope showing the surface of an enamel block prepared from a human impacted third molar tooth, on which artificial dental caries were generated and then immersed in a calcium tertiary phosphate slurry having a particle size of a maximum of 1.0 µm.
Figure 2F:
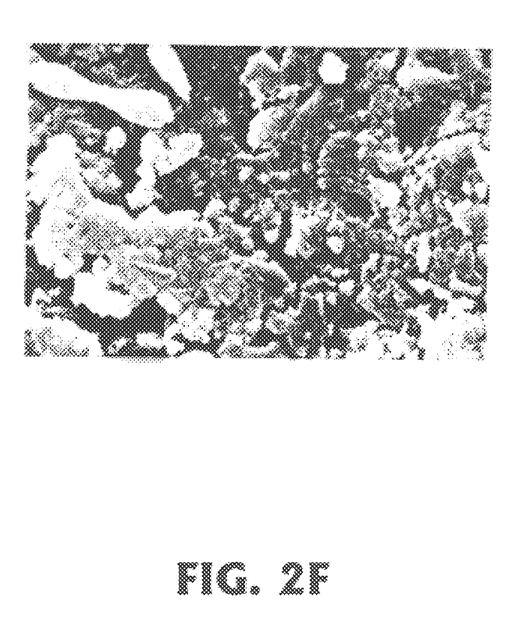
FIG. 2F is a photograph taken on a magnified scale (×3000) under an electron microscope showing the surface of an enamel block prepared from a human impacted third molar tooth, on which artificial dental caries were generated and then immersed in a calcium tertiary phosphate slurry having a particle size of more than 1.0 µm.

The above mentioned enamel blocks were immersed in three different kinds of solutions for 24 hours, namely, (a) artificial saliva (control), (d) calcium tertiary phosphate slurry of a maximum of about 1.0 $\mu$m particle size and (e) calcium tertiary phosphate slurry of more than about 1.0 $\mu$m particle size, each of which was maintained 37° C. The changes on the surface of each of the enamel blocks were observed under an electron microscope.
(4) Results obtained under electron microscope The surface of each of the enamel blocks was observed under an electron microscope (×3000) after conducting alcohol dehydration followed by a carbon casting (evaporation) using an ion sputtering device of each enamel block. The surface of the artificial dental caries portion of the control (i.e., artificial saliva was used) was found to be very rough (see FIG. 1B). On the other hand, the surface of the artificial dental caries portion of (b) (i.e., HAp slurry of a maximum of about 1.0 $\mu$m particle size was used) was found to be very smooth due to a deposition of fine particles on the dental caries portion (see FIG. 1C). Also, the surface of the artificial dental caries portion of (d) (i.e., calcium tertiary phosphate slurry of a maximum of about 1.0 $\mu$m particle size was used) was found to be smooth, although not as smooth as the above-mentioned (b) (see FIG. 2E). Deposition of particles was observed on the entire surface of the artificial dental caries portion of (c) (i.e., HAp slurry of more than about 1.0 $\mu$m particle size was used), however the surface was not as smooth as (b) (see FIG. 1D). On the surface of the artificial dental caries portion of (e) (i.e., calcium tertiary phosphate slurry of a maximum of about 1.0 $\mu$m particle size was used), although some deposition of particles was found, the surface was rather rough (see FIG. 2F).

Examples of a tooth brushing agent according to the present invention will be described in the following Examples 2 to 8. However, the present invention is not, by any means, limited to these examples and variations and modifications may be made without departing from the scope of the present invention.

Example 2
Tooth paste compound

| | |
|---|---|
| calcium pyrophosphate | 20.0 |
| hydroxyapatite | 10.0 |
| glycerin | 20.0 |
| propylene glycol | 10.0 |
| polyethylene glycol | 5.0 |
| sodium laurylsulfate | 0.8 |
| hydroxyethyl cellulose | 0.5 |
| xanthan gum | 0.5 |
| methyl parapene | 0.1 |
| sorbitol aqueous solution (70% conc.) | 3.3 |
| water | 29.8 |
| Total | 100.0 |

Example 3
Tooth paste compound

| | |
|---|---|
| aluminium hydroxide | 6.0 |
| hydroxyapatite | 50.0 |
| glycerin | 10.9 |

-continued

| | |
|---|---|
| propylene glycol | 5.0 |
| sodium laurylsulfate | 1.0 |
| carageenan | 1.0 |
| sodium benzoate | 0.1 |
| sorbitol aqueous solution (70% conc.) | 4.5 |
| water | 21.5 |
| Total | 100.0 |

Example 4
Tooth paste compound

| | |
|---|---|
| calcium tertiary phosphate | 17.0 |
| hydroxyapatite | 17.0 |
| silicic acid anhydride | 6.0 |
| glycerin | 6.0 |
| propylene glycol | 10.0 |
| sodium laurylsulfate | 1.0 |
| monofluorosodium phosphate | 0.7 |
| carageenan | 1.0 |
| butyl parapene | 0.2 |
| sorbitol aqueous solution (70% conc.) | 5.0 |
| water | 36.1 |
| Total | 100.0 |

Example 5
Tooth paste compound

| | |
|---|---|
| calcium tertiary phosphate | 35.0 |
| aluminium hydroxide | 10.0 |
| glycerin | 20.0 |
| propylene glycol | 5.0 |
| sodium laurylsulfate | 1.0 |
| carageenan | 1.0 |
| methyl parapene | 1.0 |
| menthol | 0.6 |
| sorbitol aqueous solution (70% conc.) | 2.0 |
| water | 24.4 |
| Total | 100.0 |

Example 6
Tooth liquid compound

| | |
|---|---|
| calcium tertiary phosphate | 0.1 |
| ethyl alcohol | 10.0 |
| sodium laurylsulfate | 1.0 |
| glycerin | 10.0 |
| menthol | 0.4 |
| sorbitol aqueous solution (70% conc.) | 16.6 |
| water | 61.9 |
| Total | 100.0 |

Example 7
Tooth paste compound

| | |
|---|---|
| aluminium hydroxide | 20.0 |
| silicic acid anhydride | 2.0 |
| hydroxyapatite | 0.1 |
| glycerin | 20.0 |
| propylene glycol | 10.0 |
| polyethylene glycol | 5.0 |
| sodium laurylsulfate | 0.8 |

-continued

| | |
|---|---|
| hydroxyethyl cellulose | 0.5 |
| xanthan gum | 0.5 |
| methyl parapene | 0.1 |
| sorbitol aqueous solution (70% conc.) | 5.3 |
| dextranase | 1.0 |
| water | 34.7 |
| Total | 100.0 |

Example 8
Tooth paste compound

| | |
|---|---|
| aluminium hydroxide | 20.0 |
| silicic acid anhydride | 2.0 |
| calcium tertiary phosphate | 0.1 |
| glycerin | 20.0 |
| propylene glycol | 10.0 |
| polyethylene glycol | 5.0 |
| sodium laurylsulfate | 0.8 |
| hydroxyethyl cellulose | 0.5 |
| xanthan gum | 0.5 |
| methyl parapene | 0.1 |
| sorbitol aqueous solution (70% conc.) | 5.3 |
| dextranase | 1.0 |
| water | 34.7 |
| Total | 100.0 |

It was found that all the above tooth pastes and tooth liquid were very excellent tooth brushing agents which were capable of repairing pits present on a tooth surface and protecting the tooth afterward, preventing tooth decay, strengthening teeth, and whitening teeth surfaces.

Example 9

Experiment of recalcification using tooth brushing agents (1) Experimental procedure A human maxilla second molar tooth having a white spot on the surface, which had no tooth crown repair was used for the experiment. After the root portion of the tooth was removed using a ISOMET Low Speed Saw (BUEHLER Co.), the tooth was cut in a parallel direction relative to the tooth axis so as to cut the white spot in a vertical direction. The tooth piece thus produced was polished under a continuous supply of water until its thickness became about 100 μm. The thickness of the tooth piece was confirmed by using a GS551 type gage sensor (Ono Sokki Co.).

The change in the amount of minerals (i.e., the degree of recalcification) contained in the tooth piece before and after the treatment with the tooth brushing agents was confirmed by a CMR photographing using the soft X-ray generating device CMR-2 (Softex Co.) with a 29-layered aluminium step wedge (hereinafter abbreviated as Al-SW). A microradiogram obtained for each sample was input to an EXCEL II system (Nippon Apioniques Co.) from a stereoscopic microscope SMZ-10 (Nikon Co.) using the CCD VIDEO CAMERA MODULE (SONY Ltd.) and the Al-SW was made to correspond to the amount of minerals contained using the method of Angmar et al (Studies on the Ultrastructure of Dental Enamel-IV The Mineralization of Normal Human Enamel; J. Ultrastruct. Res 8, 12–23, 1963). Based on this, a mineral isosbestic curve was obtained for each sample.

(2) Preparation of tooth brushing agent

Two kinds of tooth brushing agents containing components the same as the above Example 7 were prepared using hydroxyapatite having a maximum of 1.0 μm particle size and more than 1.0 μm, respectively. Likewise, two kinds of tooth brushing agents containing components the same as the above Example 8 were prepared using calcium tertiary phosphate having a maximum of 1.0 μm particle size and more than 1.0 μm, respectively.

(3) Experiment

Each of the above tooth brushing agents was made into a 20 wt. % suspension and the tooth piece prepared was immersed in the respective suspension. The temperature of the suspension was maintained at 36±2° C. and the immersion was continued for 40 hours. After the immersion, a CMR photographing was conducted and the images obtained were computer processed.

(4) Results

Results obtained are shown in FIGS. 3A to 6B. Each of these figures indicates a mineral isosbestic curve obtained by computer processing the CMR photographing image. In these figures, the region inside the white line indicates a portion in which the amount of minerals is less than 70%.

Figure 3A:
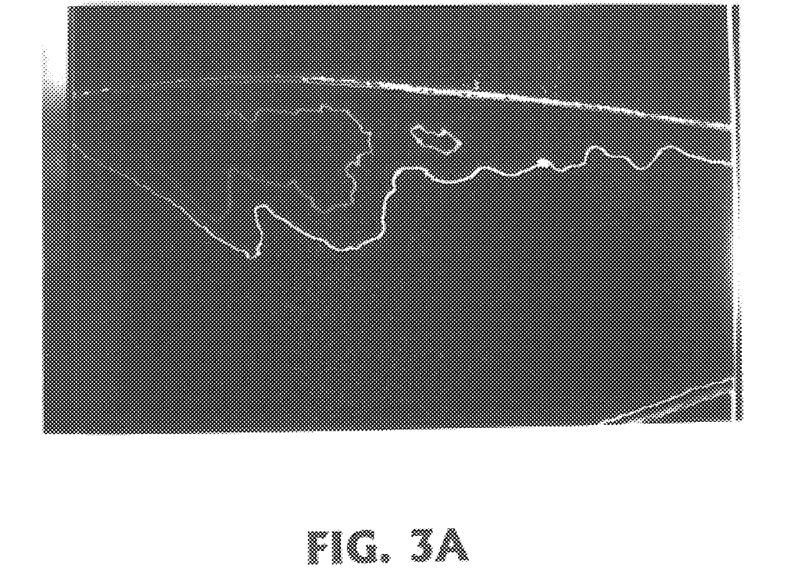
FIG. 3A is a mineral isosbestic curve of a human maxilla second molar tooth piece sample before the treatment with a tooth brushing agent, obtained by computer processing a CMR photographing image, for showing the amount of minerals contained in the sample, in which the region inside the white line indicates the amount of minerals to be less than 70%.
Figure 3B:
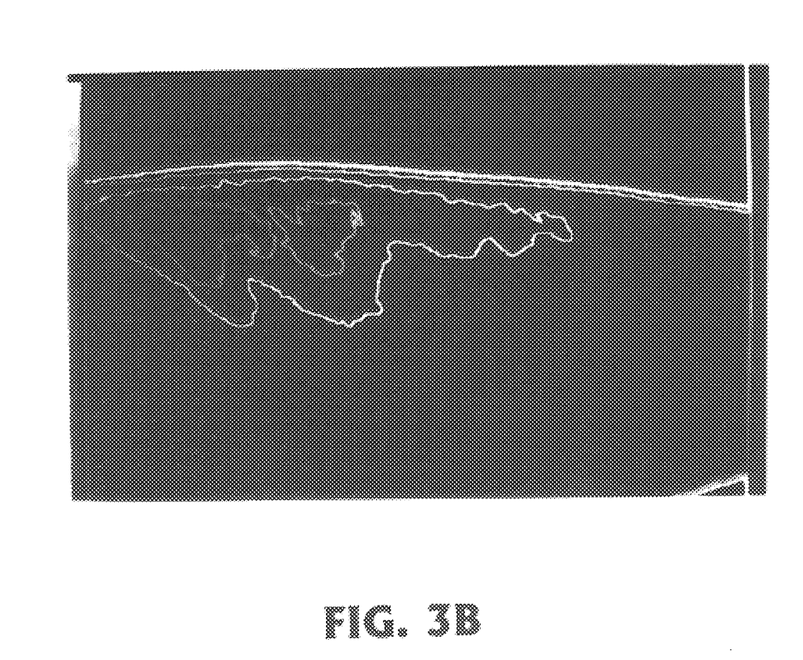
FIG. 3B is a mineral isosbestic curve of a human maxilla second molar tooth piece sample after the treatment with a tooth brushing agent having the same components described in Example 7 in which hydroxyapatite having a minimum of 1.0 µm particle size was used, obtained by computer processing a CMR photographing image, for showing the amount of minerals contained in the sample, in which the region inside the white line indicates the amount of minerals to be less than 70%.
Figure 4A:
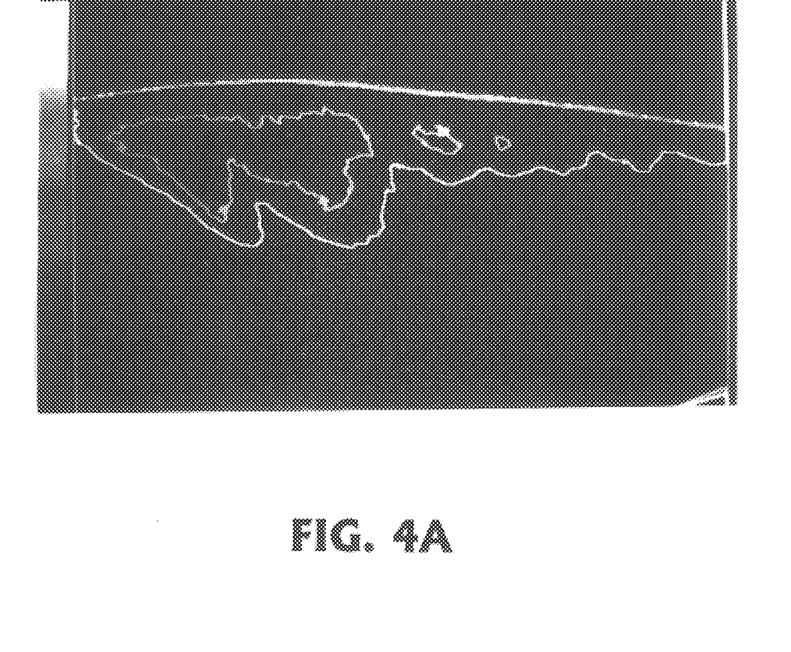
FIG. 4A is a mineral isosbestic curve of a human maxilla second molar tooth piece sample before the treatment with a tooth brushing agent, obtained by computer processing a CMR photographing image, for showing the amount of minerals contained in the sample, in which the region inside the white line indicates the amount of minerals to be less than 70%.
Figure 4B:
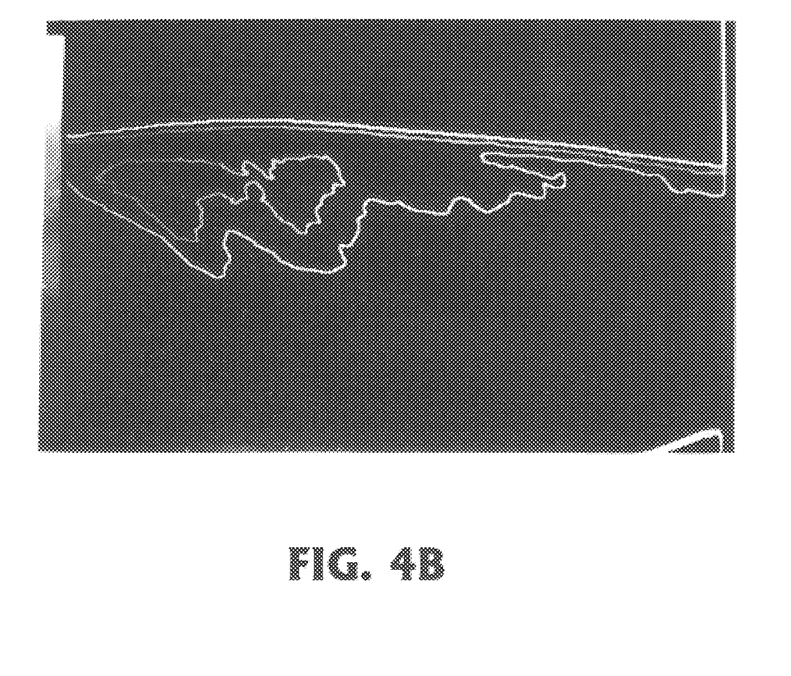
FIG. 4B is a mineral isosbestic curve of a human maxilla second molar tooth piece sample after the treatment with a tooth brushing agent having the same components described in Example 7 in which hydroxyapatite having a more than 1.0 µm particle size was used, obtained by computer processing a CMR photographing image, for showing the amount of minerals contained in the sample, in which the region inside the white line indicates the amount of minerals to be less than 70%.

FIGS. 3A and 3B show the effect of the tooth brushing agent containing hydroxyapatite having a maximum of 1.0 μm particle size. FIG. 3A shows the condition of the tooth piece before the immersion treatment and FIG. 3B indicates that of the tooth piece after the immersion treatment. Likewise, FIGS. 4A and 4B show the effect of the tooth brushing agent containing hydroxyapatite having a particle size of more than 1.0 μm. FIG. 4A shows the condition of the tooth piece before the immersion treatment and FIG. 4B indicates that of the tooth piece after the immersion treatment.

Figure 5A:
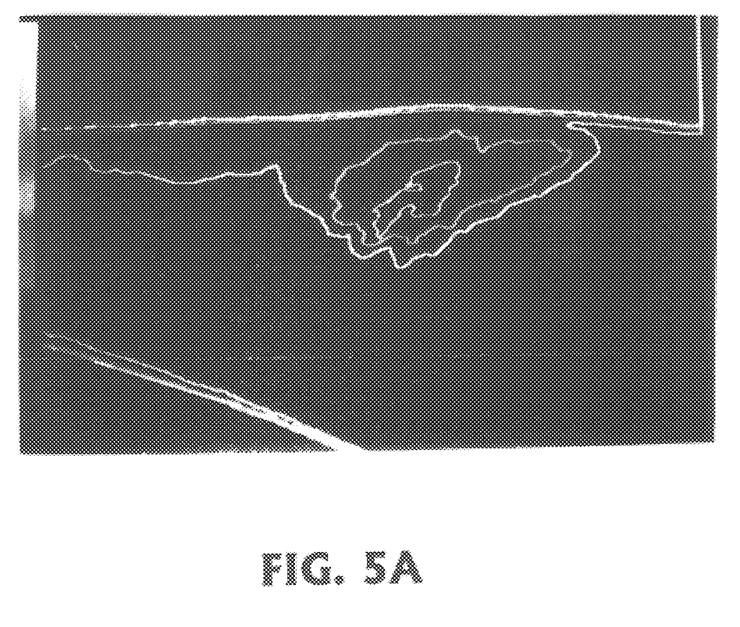
FIG. 5A is a mineral isosbestic curve of a human maxilla second molar tooth piece sample before the treatment with a tooth brushing agent, obtained by computer processing a CMR photographing image, for showing the amount of minerals contained in the sample, in which the region inside the white line indicates the amount of minerals to be less than 70%.
Figure 5B:
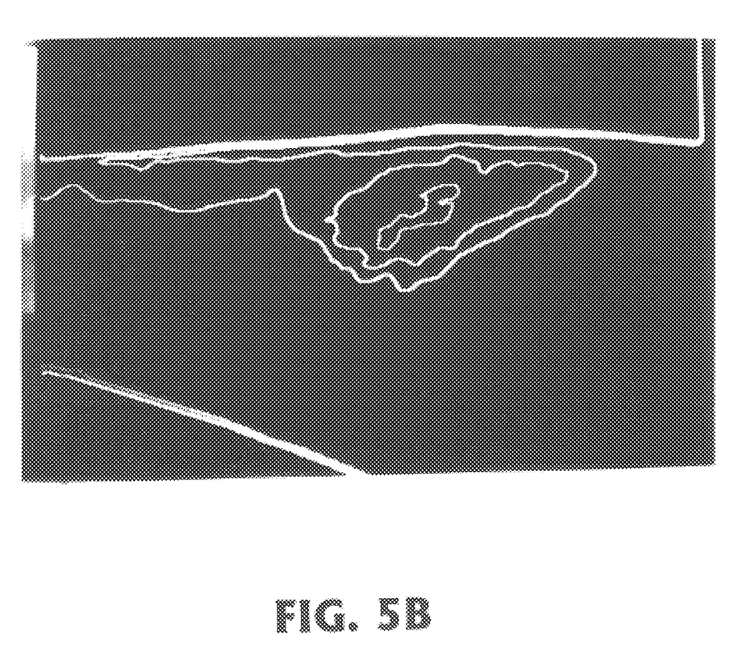
FIG. 5B is a mineral isosbestic curve of a human maxilla second molar tooth piece sample after the treatment with a tooth brushing agent having the same components described in Example 8 in which calcium tertiary phosphate having a minimum of 1.0 µm particle size was used, obtained by computer processing a CMR photographing image, for showing the amount of minerals contained in the sample, in which the region inside the white line indicates the amount of minerals to be less than 70%.
Figure 6A:
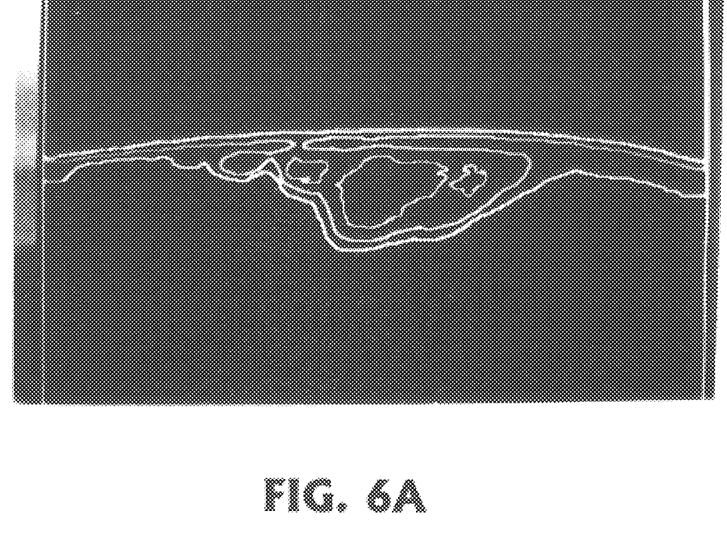
FIG. 6A is a mineral isosbestic curve of a human maxilla second molar tooth piece sample before the treatment with a tooth brushing agent, obtained by computer processing a CMR photographing image, for showing the amount of minerals contained in the sample, in which the region inside the white line indicates the amount of minerals to be less than 70%.
Figure 6B:
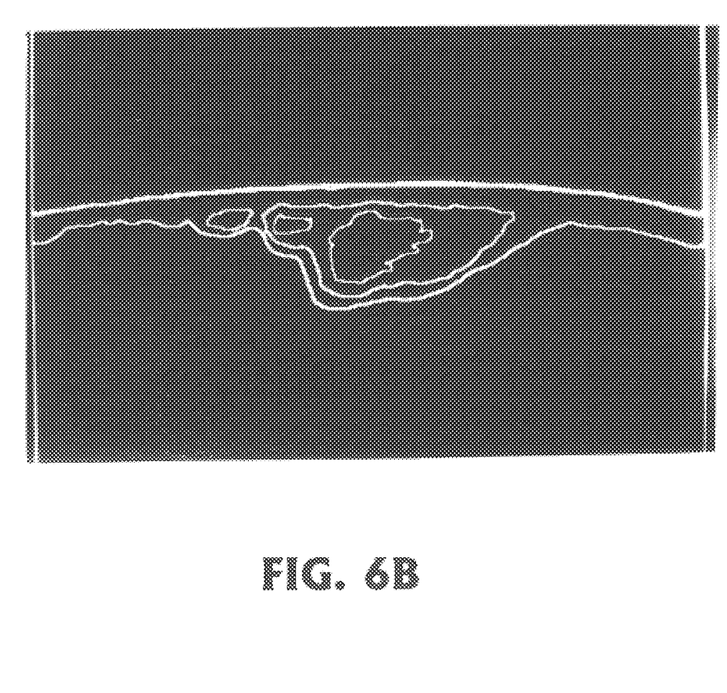
FIG. 6B is a mineral isosbestic curve of a human maxilla second molar tooth piece sample after the treatment with a tooth brushing agent having the same components described in Example 8 in which calcium tertiary phosphate having a more than 1.0 µm particle size was used, obtained by computer processing a CMR photographing image, for showing the amount of minerals contained in the sample, in which the region inside the white line indicates the amount of minerals to be less than 70%.

FIGS. 5A and 5B show the effect of the tooth brushing agent containing calcium tertiary phosphate having a maximum of 1.0 μm particle size. FIG. 5A shows the condition of the tooth piece before the immersion treatment and FIG. 5B indicates that of the tooth piece after the immersion treatment. Likewise, FIGS. 6A and 6B show the effect of the tooth brushing agent containing calcium tertiary phosphate having a particle size of more than 1.0 μm. FIG. 6A shows the condition of the tooth piece before the immersion treatment and FIG. 6B indicates that of the tooth piece after the immersion treatment.

From FIGS. 3A to 6B, it is obvious that the tooth brushing agent containing hydroxyapatite having a maximum of 1.0 μm particle size is most effective for recalcification and the tooth brushing agent containing calcium tertiary phosphate having a maximum of 1.0 μm particle size has the second largest effect on recalcification. On the other hand, the tooth brushing agent containing hydroxyapatite having a particle size of more than 1.0 μm has a low effect on recalcification, and the tooth brushing agent containing calcium tertiary phosphate having a particle size of more than 1.0 μm has almost no effect on recalcification.

What is claimed is:

1. A composition for dental tissue comprising:
   hydroxyapatite having a particle size of a maximum of about 1.0 μm and a humectant.

2. The composition for dental tissue as claimed in claim 1, wherein the particle size of said hydroxyapatite is in a range from about 0.05 μm to about 1.0 μm.

3. The composition for dental tissue as claimed in claim 1, wherein the amount of said hydroxyapatite is a minimum of 0.1 percent by weight.

4. A tooth brushing agent comprising:
   hydroxyapatite having a particle size of a maximum of about 1.0 μm and a humectant.

5. The tooth brushing agent as claimed in claim 4, wherein the particle size of said hydroxyapatite is in a range from about 0.05 μm to about 1.0 μm.

6. The tooth brushing agent as claimed in claim 4, wherein the amount of said hydroxyapatite is a minimum of 0.1 percent by weight.

* * * * *